(12) United States Patent
MacLaughlan

(10) Patent No.: US 12,016,941 B2
(45) Date of Patent: Jun. 25, 2024

(54) TREATMENT COMPOSITION FOR NASAL AND ORAL DRYNESS, NOSEBLEEDS, AND ALLERGY SYMPTOMS

(71) Applicant: Profounda Health and Beauty Inc., Orlando, FL (US)

(72) Inventor: Todd Ewen MacLaughlan, Orlando, FL (US)

(73) Assignee: Profounda Health and Beauty Inc., Orlando, FL (US)

( * ) Notice: Subject to any disclaimer, the term of this patent is extended or adjusted under 35 U.S.C. 154(b) by 0 days.

(21) Appl. No.: 17/685,574

(22) Filed: Mar. 3, 2022

(65) Prior Publication Data

US 2023/0277424 A1  Sep. 7, 2023

(51) Int. Cl.

| A61K 8/34 | (2006.01) |
|---|---|
| A61K 8/04 | (2006.01) |
| A61K 8/19 | (2006.01) |
| A61K 8/86 | (2006.01) |
| A61K 9/00 | (2006.01) |
| A61K 31/047 | (2006.01) |
| A61K 47/02 | (2006.01) |
| A61K 47/10 | (2017.01) |
| A61K 47/18 | (2017.01) |
| A61K 47/34 | (2017.01) |

(52) U.S. Cl.
CPC ............. *A61K 8/345* (2013.01); *A61K 8/042* (2013.01); *A61K 8/19* (2013.01); *A61K 8/86* (2013.01); *A61K 9/0056* (2013.01); *A61K 31/047* (2013.01); *A61K 47/02* (2013.01); *A61K 47/10* (2013.01); *A61K 47/186* (2013.01); *A61K 47/34* (2013.01); *A61K 2800/48* (2013.01); *A61K 2800/524* (2013.01)

(58) Field of Classification Search
CPC .......... A61K 8/345; A61K 8/042; A61K 8/19; A61K 8/86; A61K 9/0056; A61K 31/047; A61K 47/02; A61K 47/10; A61K 47/186; A61K 47/34; A61K 2800/48; A61K 2800/524

USPC ......................................................... 424/401
See application file for complete search history.

(56) References Cited

U.S. PATENT DOCUMENTS

| 6,054,143 | A | * | 4/2000 | Jones | ................... | A61K 31/047 |
|---|---|---|---|---|---|---|
| | | | | | | 514/23 |
| 2014/0142126 | A1 | * | 5/2014 | Chen | ....................... | A61P 29/00 |
| | | | | | | 544/280 |
| 2015/0010654 | A1 | * | 1/2015 | Arnold | ................. | A61K 31/198 |
| | | | | | | 424/717 |

FOREIGN PATENT DOCUMENTS

WO  WO-2011141929 A2 * 11/2011 ........... A61K 31/335

OTHER PUBLICATIONS

"Rhinase Allergy Relief Lubricating Nasal Gel—Steroid Free, Dual Wetting Agent & Salt Formulation (1 oz.) for Nasal Dryness Nosebleeds Saline Gel for Nose"; https://www.amazon.com/Rhinase-Lubricating-Allergy-Prevent-Nosebleeds/dp/B015DEYJJU; Mar. 21, 2017. Accessed Feb. 3, 2023. (Year: 2017).*

"Rhinase Allergy Relief Saline Nasal Spray—Steroid Free, Dual Wetting Agent & Salt Formulation, 300 Sprays for Dry Nose, Allergy, nosebleeds from Nasal Dryness"; https://www.amazon.com/Rhinase-Allergy-Relief-Saline-Nasal/dp/B015DEYIHI; Apr. 1, 2016. Accessed Feb. 3, 2023. (Year: 2016).*

* cited by examiner

*Primary Examiner* — Frederick F Krass
*Assistant Examiner* — Lucy M Tien
(74) *Attorney, Agent, or Firm* — Dentons Cohen & Grigsby P.C.

(57) ABSTRACT

The invention discloses a treatment composition to treat nasal or oral dryness and allergy symptoms, and a method for using the same. Certain compositions include xylitol, at least two wetting agents, an aqueous carrier, and other active ingredients, such as a potassium salt, a sodium salt, and a preservative. The composition may be configured as a nasal or oral spray, and oral rinse, or a nasal gel.

2 Claims, No Drawings

TREATMENT COMPOSITION FOR NASAL AND ORAL DRYNESS, NOSEBLEEDS, AND ALLERGY SYMPTOMS

FIELD OF THE INVENTION

The present disclosure relates to a nasal or oral treatment composition, wherein application of the composition in and around the nasal cavity or oral cavity treats nasal dryness, oral dryness, and allergy symptoms.

BACKGROUND OF THE INVENTION

The nostrils and sinuses (nasal passages) are air-filled hollow cavities in the skull that are present around the forehead, cheeks, and nose. In a healthy nasal passage, a thin layer of mucus lines the sinuses to retain moisture and trap debris, pollen and bacteria, fungi, etc., which may help limit sinus dryness and irritation. However, if the nasal passages are not properly lined with this mucus layer, the sinuses can become dry, leading to a feeling of uncomfortable dryness in the nose and airways, swelling, sinus infections, and nosebleeds. The body may also produce excess mucus to rehydrate the nasal mucosa leading to further congestion and irritation.

Moreover, dry sinuses and dry nasal passages may be attributed to allergic rhinitis, or inflammation of the nasal mucosa membrane. Allergic rhinitis causes the body's immune system to view harmless airborne particles as potentially hazardous—prompting the body to release histamine and other mediators that cause an allergic response. Statistical studies have shown that symptoms related to nasal dryness and allergies affect a large portion of the world's population each year, with estimates of 400 to 500 million people suffering from allergic rhinitis alone.

Xylitol, a purported bacteriostatic agent, has been recognized as possessing certain therapeutic functions. Particularly well recognized are its added benefits to nasal preparations. It has been demonstrated that use of a nasal spray with xylitol is effective in washing the nasal mucosa and flushing away harmful bacteria and pollutants that might otherwise lead to sinusitis, ear infections, and/or upper respiratory disease. Accordingly, use of xylitol has been shown to have moisturization benefits by decreasing nasal dryness to a greater degree than regular saline compositions leading to lower amounts of congestion. Wetting agents, or surfactants, have also proven to be beneficial in nasal and oral preparations as effective moisturizers. They have the dual effect of preventing evaporation by creating a protective barrier and by retaining moisture in the oral and nasal passage while relieving mucosa irritation.

Several problems have heretofore plagued the field of nasal treatment compostions used to treat nasal dryness and allergy symptom relief. One such problem is the failure of prior nasal compositions to provide adequate relief of nasal dryness and congestion for a desired time interval. Another pertinent issue arises when the pH levels of the compositions are not fully optimized for the nose (pH 6.0-6.4). When pH levels in the nose are not ideal, fungal infections may occur or the full benefit in the co-use of a steroidal nasal spray may be precluded. The steroidal nasal spray relies on a certain pH level for maximum diffusion into the nasal mucosa, thereby affecting effectiveness of the steroid.

Accordingly, it is an object of the present disclosure to formulate a nasal treatment composition that optimizes combinations of wetting agents, pH, salt concentration and xylitol to provide a nasal treatment composition that is better distributed to a patient's tissues and allows for maximum moisture retention and dispersion of the bacteriostatic agent xylitol, the wetting agents and the salts in the nasal cavity.

SUMMARY OF THE INVENTION

The present invention overcomes the shortcomings of the prior art by combining two to three approaches into a single nasal or oral treatment composition. That is, utilizing at least two wetting agents to create a protective barrier to retain moisture in the nasal mucosa or oral cavity; xylitol that acts as a moisturizer/bacteriostatic agent; and a dual salt formulation that works with the body's natural sodium potassium pump, to retain additional moisture. The configurations of the present disclosure may be adaptable for use as either a nasal spray, nasal gel, oral spray, or oral mist (e.g., mouth wash or mouth rinse).

Accordingly, the present disclosure comprises at least two wetting agents, xylitol, dual salts ($Na^+$ and $K^+$ salts), and an aqueous carrier at a certain pH level, wherein application of the composition to the nasal cavity for application in and around the nasal mucosa treats nasal dryness, nosebleeds, and allergy symptoms. Alternatively, application to the oral cavity may treat oral dryness.

According to certain aspects of the present disclosure, the at least two wetting agents may comprise polyethylene glycol and propylene glycol, wherein the wetting agents are provided in the composition in a total amount of 10.0 wt. % to 50 wt. % based on a total wt. % of the composition.

According to certain aspects of the present disclosure, the at least two wetting agents may comprise 8 wt. % to 20 wt. % polyethylene glycol and 2 wt. % to 30 wt. % propylene glycol based on a total wt. % of the composition.

According to certain aspects of the present disclosure, the xylitol is provided in the composition at 0.1 wt. % to 5 wt. % based on a total wt. % of the composition.

According to certain aspects of the present disclosure, the xylitol is provided in the composition at 3 wt. % to 4.5 wt. % based on a total wt. % of the composition.

According to certain aspects of the present disclosure, a sodium salt and a potassium salt may be added to the treatment composition, wherein the sodium salt and the potassium salt comprise sodium chloride and potassium chloride each provided in the composition at 0.05 wt. % to 1.0 wt. % based on a total wt. % of the composition.

According to certain aspects of the present disclosure, a preservative may be added to the treatment composition. Exemplary preservatives comprise benzalkonium chloride and/or sorbic acid provided in the composition at 0.01 wt. % to 0.5 wt. % based on a total wt. % of the composition.

According to certain aspects of the present disclosure, the preservative comprises sorbic acid provided in the composition at 0.01 wt. % to 0.3 wt. % based on a total wt. % of the composition. According to certain aspects of the present disclosure, the preservative comprises benzalkonium chloride provided in the composition at 0.01 wt. % to 0.2 wt. % based on a total wt. % of the composition.

According to certain aspects of the present disclosure, the aqueous carrier comprises purified water provided in the composition at 25 wt. % to 89.9 wt. % based on a total wt. % of the composition, and one or more thickening agents.

In some such embodiments, the treatment composition may be configured as a nasal spray, oral spray, or oral rinse, wherein the one or more thickening agents may comprise glycerin provided in the nasal treatment composition at 2 wt. % to 10 wt. % based on a total wt. % of the composition.

In other such embodiments, the treatment composition may be configured as a nasal gel, wherein the one or more thickening agents may be selected from the group consisting of glycerin, a high molecular weight crosslinked polyacrylic acid polymer such as Carbopol© (e.g., Carbopol© 974P), carboxymethylcellulose sodium, and combinations thereof provided in the composition at 5 wt. % to 25 wt. % based on a total wt. % of composition.

According to certain aspects of the present disclosure, a buffer is added to the treatment composition, wherein the at least one buffer may be selected from the group consisting of dibasic sodium phosphate anhydrous, potassium phosphate monobasic, or a combination thereof.

According to certain aspects of the present disclosure, the treatment composition has a pH of 5.5 to 7.5.

According to certain aspects of the present disclosure, the treatment composition has a pH of 6.0 to 6.5.

Accordingly, the present disclosure may be administered to the subject as a liquid formulation such as a nasal spray, mist, or via a nebulizer, or as an oral spray or rinse, or alternatively as a thickened formulation such as a nasal gel.

The objects of the present invention will be realized and attained by means of the combinations specifically outlined in the appended claims. The foregoing general description and the following detailed description of this invention are provided to illustrate various aspects of the present invention, and by no means are to be viewed as limiting any of the described embodiments.

Definitions and Abbreviations

Throughout this description and in the appended claims, use of the singular includes the plural and plural encompasses singular, unless specifically stated otherwise. For example, although reference is made herein to "a" composition, or "the" aqueous carrier, one or more of any of these components and/or any other components described herein may be used.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a composition comprising xylitol, at least two wetting agents, and an aqueous carrier, a composition "consisting essentially of" or "consisting of" xylitol, at least two wetting agents, and an aqueous carrier is also within the present scope. In this context, "consisting essentially of" means that any additional components will not materially affect the efficacy of the method.

Moreover, other than where indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations and reported as precisely as possible, any numerical value inherently contains certain errors necessarily resulting from the standard variation found in their respective testing measurements. When ranges are given, any endpoints of those ranges and/or numbers within those ranges can be combined within the scope of the present invention.

"Synergistic combinations" or "synergistic effects", as used herein, are combinations of xylitol and certain wetting agents to achieve an antibacterial synergistic effect in which wetting agents are used to maximally moisturize the nasal cavity while fully dispersing xylitol throughout the nasal mucosa, or to maximally moisturize the oral cavity. Synergistic combinations of xylitol and wetting agents may provide for an improved therapeutic effectiveness, which may be measured by a reduction in the total amount of bacteria that may be present (e.g., *Streptococcus pneumonia* or other forms) or a length of time of nasal or oral dryness or allergy symptoms, or an improvement in other indicators of patient health. Synergistic combinations of the present disclosure may combine a therapeutically effective amount of xylitol with a therapeutically effective amount of at least the two desired wetting agents.

"Treat" or "treatment" refers to therapeutic treatment wherein the object is to slow down (lessen) an undesired physiological change (e.g., allergic reaction, inflammation, nasal or oral dryness) or disease, or to provide a beneficial or desired clinical outcome during treatment. Those in need of treatment include those subjects already presenting with the undesired physiological change or disease as well as those subjects prone to have the physiological change or disease (e.g., a patient with rhinitis who is developing symptoms of sinusitis).

As used herein, the term "allergy symptoms" may be understood to include sneezing, congestion, runny nose, itchiness of the eyes, nose, and throat, and the like. While specific symptoms have been listed, others known in the art are within the scope of the present disclosure.

The phrase "therapeutically effective amount" as used herein refers to an amount sufficient to provide treatment as defined herein and may include an amount effective to inhibit bacteria growth associated with nasal or oral dryness or allergy symptoms, e.g., chronic rhinosinusitis or allergic rhinitis. As such, a therapeutically effective amount may refer to a sufficient amount of the composition to provide the desired biological, therapeutic, and/or prophylactic result. The desired results include elimination of nasal or oral dryness or allergy symptoms or reduction and/or alleviation of the signs, symptoms, or causes of nasal or oral dryness or allergy symptoms, or any other desired alteration of a biological system, such as indicated above with regard to synergistic combinations or synergistic effects. In relation to a pharmaceutical or veterinary composition, effective amounts can be dosages that are recommended in the modulation of a diseased state or signs or symptoms thereof. Effective amounts may differ depending on the composition used and the route of administration employed. Effective amounts are routinely optimized taking into consideration various factors of a particular patient, such as age, weight, gender, etc. and the area affected by the disease- or disease-causing nasal or oral dryness or allergy symptoms.

"Patient" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. "Patient" and "subject" are used interchangeably herein.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

DETAILED DESCRIPTION OF THE INVENTION

The present invention comprises a treatment composition to treat nasal or oral dryness and allergy symptoms. Disclosed herein are various compositions, comprised of xylitol, at least two wetting agents, an aqueous carrier, dual salts, and optionally other active and/or inactive ingredients, that may be provided in nasal sprays, oral sprays or rinses, and/or nasal gels otherwise delivered into a subject's nasal cavity and/or sinus passages.

The presently disclosed compositions and methods may be used to relieve dryness and irritation in and around the nasal or oral passages caused by the following: environmental conditions, including, without limitation, dry room air, low humidity, and winter dryness; allergic rhinitis, including, without limitation, seasonal allergic rhinitis, perennial allergic rhinitis, and non-allergic rhinitis; acute, recurrent or chronic sinusitis (or more formally known as rhinosinusitis); traveling; nose bleeds; common-colds; the flu; non-invasive ventilation (NIV) therapies, including, without limitation, continuous positive airway pressure (CPAP) therapy and bilevel positive airway pressure (BiPAP) therapy; oxygen therapy; other medications; and drug and non-drug therapies, including, without limitation, anti-histamines, prescription drugs, and natural products (i.e. garlic).

The presently disclosed compositions and methods may also allow for an increase in the ciliary beat frequency of nasally congested patients, in turn resulting in the increase of nasal mucociliary clearance times. The ciliary beat frequency (CBF) has been found to increase after the addition of small amounts of potassium chloride and/or certain wetting agents, such as propylene glycol. This indicates that the presence of both sodium, potassium, and even certain wetting agents may stimulate ciliary movement and improve functioning of the mucociliary clearance in the nose.

Accordingly, certain active ingredients of the presently disclosed compositions may further include sodium and potassium salts, and buffers to maintain the pH within an optimal range for the nasal mucosa and to allow co-administration with other therapeutic agents, e.g., steroids.

In order to make the technical problem solved by the present disclosure, and for the technical scheme and the beneficial effects to be more clearly understood, the invention is further described in detail herein. It should be understood that the specific embodiments described herein are only used for explaining the invention rather than limiting the invention. In addition, it is anticipated that alternative embodiments and implementations may be made into suspensions, lozenges, tablets, capsules, topical formulations, and/or ingestible products, such as teas or other beverages, for example. In a specific preferred embodiment, the composition may be formulated as an oral spray, oral mist, or in an application similar to mouth wash or mouth rinse. According to certain aspects, the oral spray or oral mist could be found to migrate or disperse to the nasal mucosa, providing treatment similar to the nasal spray or nasal gel.

Xylitol is a pentitol (five-carbon sugar alcohol) having meso-configuration, being derived from xylose by reduction of the carbonyl group, represented by the formula (I). The empirical formula is $C_5H_{12}O_5$, yielding a molecular weight of 152.15 g/mol. Xylitol is a colorless or white crystalline solid that is soluble in water. It can be classified as a polyalcohol and a sugar alcohol, specifically an alditol.

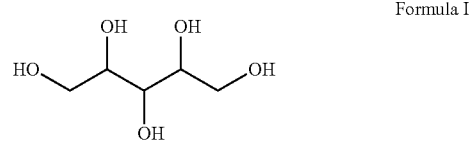

Formula I

Xylitol has been demonstrated to possess various therapeutic benefits and may provide a synergistic effect with other ingredients of a formulation in treating and/or preventing viral infections. In particular, xylitol has been found to be remarkably effective in eradicating microbes, such as bacteria and viruses, and in moisturizing nasal and oral passages, sinuses, and the like. Without being limited by theory, this is thought to occur because xylitol can create a hyper-osmotic solution that pulls moisture toward it from surrounding tissues without generated mucous. Thus, the combination of xylitol with other ingredients may result in a decrease in mucous production, potentially along with accompanying anti-bacterial, anti-viral and other health benefits associated with xylitol. Xylitol may also enhance the taste and/or reduce the negative smell/aftertaste issues commonly associated with prior art formulations. Moreover, by providing a sweetener that does not include sugar and serves as an active agent in the formulation, several benefits may be derived. For example, although xylitol acts as a sweetener, unlike typical sweeteners, xylitol enhances the ability of other agents to treat bacterial infections by actively starving the microorganisms causing the symptoms, rather than one that counteracts the active ingredients in a nasal or oral sprays or other treatment compositions by feeding the microorganisms, or one that only passively starves the microorganisms by providing a sweetener that is not consumed by the more common oral and pharyngeal pathogens. Thus, compositions including xylitol may result in improved ability to treat various symptoms that may be caused by microorganisms (along with others not caused by microorganisms) and, more importantly, to moisturize and fight the bacterial, viral, and/or other microorganisms behind these symptoms.

The present inventor has demonstrated that the combination of xylitol, with wetting agents and an aqueous carrier, has an even greater effect in treating nasal and oral dryness and allergy symptoms than the prior art. A wetting agent is a surface-active molecule used to reduce the surface tension of water. The high surface tension of water is problematic in many applications whereby spreading of water is needed. Wetting agents increase the spreading and penetrating properties of a liquid by lowering its surface tension, or the tendency of its molecules to adhere to each other at the surface. Wetting agents can be made up of a variety of chemicals, all of which have this tension-lowering effect. As such, studies have shown wetting agents to be effective in dispersing steroids in steroidal sprays to avoid over concentration and to create a protective barrier from nasal irritants.

Accordingly, wetting agents have the dual effect of preventing evaporation by retaining moisture in the nasal passage while relieving nasal mucosa irritation.

In preferred embodiments, the treatment composition may comprise at least two wetting agents. According to certain preferred aspects, the at least two wetting agents have different wetting angles or other physiochemical properties. Exemplary wetting agents comprise polyethylene glycol and propylene glycol, which may be included in a total amount of 10 to 50 percent by weight based on the total weight of the composition. The present inventor has found that this unique combination of wetting agents does not smell, which is an important aspect for a nasal or oral preparation, and provides the best combination of wetting angles and thus maximizes the spread and moisturizing ability of the composition while also providing the best 'nose feel' (i.e., is not overly thick and sticky, or slimy).

According to certain aspects, polyethylene glycol may be present in amounts of at least 8 percent by weight, such as at least 9, 10, 11, 12, 13, 14, or 15 percent by weight based on the total weight of the composition. Polyethylene glycol may be present in amounts up to 20 percent by weight, such as up to 19, 18, 17, 16, 15, 14, 13, 12, or 10 percent by weight based on the total weight of the composition. Any combination of the lower and upper amounts of polyethylene glycol may be included in the composition and is within the scope of the present disclosure. For example, polyethylene glycol may be present in amounts of 8 to 10, or 10 to 25, or 10 to 20 percent by weight based on the total weight of the composition. According to certain preferred aspects, polyethylene glycol may be present in amounts of 8 percent by weight to 20 percent by weight, such as 15 percent by weight, based on the total weight of the composition.

Polyethylene glycols (PEGs) are linear polymers formed by the addition reaction of ethylene glycol with ethylene oxide and are commercially available in average molecular weights ranging from about 200 to greater than 20,000. The commercially available grades of polyethylene glycol are marketed based on the average molecular weight, i.e. the grade nomenclature is identified with the molecular weight. For example, PEG 400 represents material with an average molecular weight of 400 and the material with an average molecular of 600 is known as PEG 600. PEG 200, 300, 400, and 600 are clear viscous liquids at room temperature; PEG 900, 1000, 1450, 3350, 4500 and 8000 are white, waxy solids. Preferred polyethylene glycols for the compositions disclosed herein are PEG 400 to PEG 3350. More preferred polyethylene glycol is granular PEG 3300 or PEG 3350.

According to certain aspects, propylene glycol may be present in amounts of at least 2 percent by weight, such as at least 3, 4, 5, 6, 7, 8, 9, 10, 11, 12, 13, 14, 15, 16, 17, 18, 19, or 20 percent by weight based on the total weight of the composition. Propylene glycol may be present in amounts up to 30 percent by weight, such as up to 29, 28, 27, 26, 25, 24, 23, 22, 21, 20, 19, 18, 17, 16, 15, 14, 13, 12, 11, or 10 percent by weight based on the total weight of the composition. Any combination of the lower and upper amounts of propylene glycol may be included in the composition and is within the scope of the present disclosure. For example, propylene glycol may be present in amounts of 2 to 10, or 15 to 25, or 10 to 20 percent by weight based on the total weight of the composition. According to certain preferred aspects, propylene glycol may be present in amounts of propylene 2 to 30 percent by weight, such as 5 percent by weight or 20 percent by weight, based on the total weight of the composition.

In some embodiments, the treatment composition may comprise other forms of suitable wetting agents, such as vegetable glycerin, phytosqualan, coco glucoside, biophytosebum, decyl glucoside, lauryl glucoside, sucrose cocoate, caprylyl, caprylyl/capryl glucoside 10-20%, or a combination thereof.

The treatment composition contains xylitol in amounts of at least 0.1 percent by weight, such as at least 0.5, 1, 1.5, 2, 2.5, or 3 percent by weight, based on the total weight of the composition. The treatment composition contains xylitol in amounts up to 15 percent by weight, such as up to 14, 13, 12, 11, 10, 9, 8, 7, 6, 5, or 4 percent by weight based on the total weight of the composition. Any combination of the lower and upper amounts of xylitol may be used in the composition and is within the scope of the present disclosure. For example, xylitol may be present in amounts of 0.1 to 12, or 2 to 11, or 0.1 to 5 percent by weight based on the total weight of the composition. According to certain preferred aspects, xylitol may be present in amounts of 0.1 to 5 percent by weight. Most preferably, xylitol may be present in amounts of 3 to 4.5 percent by weight based on the total weight of the composition. Xylitol, in combination with the at least two wetting agents, may enhance the synergistic effects referenced elsewhere herein.

The present inventors further realized that the effectiveness of the presently disclosed treatment compositions comprising at least two wetting agents and xylitol could be significantly improved by formulation in a suitable buffer or pH adjusted composition. Such buffers may provide pH levels suitable for more effective co-use of steroids and other therapeutic formulations and may further improve distribution or adsorption of the xylitol within the nasal mucosa.

Accordingly, the treatment composition may be configured to maintain a desired pH level, such as by addition of at least one buffer and/or an acid or base. According to certain aspects, the at least one buffer is in the form of dibasic sodium phosphate anhydrous, potassium phosphate monobasic, or a combination thereof. According to certain other aspects, the pH of the composition may be adjusted with a base, such as a hydroxide, e.g., sodium or potassium hydroxide. As such, the nasal treatment composition has a pH level of 5.5 to 7.5, preferably a pH level of 5.8 to 6.5, and most preferably, a pH level is between 6.0 and 6.4.

Further, the treatment composition may contain both a sodium salt and a potassium salt. Most preferably, the sodium salt and potassium salt are added in the form of sodium chloride and potassium chloride, each of which may be included in amounts of 0.05 to 1.0 percent by weight based on the total weight of the composition. In some embodiments, the nasal treatment composition may further comprise additional other forms of suitable salts, such as magnesium chloride and/or calcium chloride.

The treatment composition may contain a preservative, which may be selected from benzalkonium chloride or sorbic acid. The preservative may be present in amounts of 0.005 to 0.5 percent weight based on the total weight of the composition.

In preferred embodiments, the preservative is benzalkonium chloride present in the amounts of 0.01 to 0.3 percent weight based on the total weight of the composition. In some embodiments, the treatment composition may be comprised of other forms of preservatives, such as olive leaf extract, potassium sorbate (below pH 6), biosecuris (citrus extracts), rosemary extract, *lactobacillus* ferment, *magnolia* bark extract, cranberry juice powder, chlorphensin, grapefruit seed extract, *eucalyptus* oil, or a combination thereof.

The treatment composition contains an aqueous carrier comprised of purified water in amounts of 25 to 89.9 percent weight based on the total weight of the composition.

According to certain aspects, the treatment composition may optionally comprise one or more thickening agents. Exemplary thickening agents include glycerin, a high molecular weight crosslinked polyacrylic acid polymer such as Carbopol©, carboxymethylcellulose sodium, xanthan gum, guar gum, bentonite, magnesium aluminum silicate (pH 9-10), kelp extract, cassava powder, agar agar (pH 6.5-7.5), vegetable glycerin, *papaya* fruit peel extract, glucomannan, sodium alginate, *sclerotium* gum, soy lecithin, acacia gum (pH 4.4), cellulose gum, *Ccimum basilicum*, *salvia hispanica* (chia), biosaccharide gum-1, *Oryza sativa* starch, carrageenan, tribehinin, arrowroot, glycol stearate, sodium hyaluronate, cetearyl alcohol, glyceryl stearate, dexpanthenol, propolis extract, or a combination thereof. According to preferred aspects, the one or more thickening agents may be selected from the group consisting of glycerin, a Carbopol© homopolymer (e.g., an acrylic acid crosslinked with allyl sucrose or allyl pentaerythritol, such as Carbopol© 974P), carboxymethylcellulose sodium, and combinations thereof.

In one embodiment, in which the treatment composition is configured as a nasal spray or oral spray or rinse, the treatment composition contains one or more thickening agents included in the amounts of 2 to 10 percent weight based on the total weight of the composition. According to preferred aspects, the one or more thickening agents included in the nasal or oral spray comprise glycerin.

In one embodiment, in which the treatment composition is configured as an oral spray or rinse, the treatment composition may further comprise colorants and flavorings as commonly known in the art.

In another embodiment, in which the treatment composition is configured as a nasal gel, the treatment composition contains one or more thickening agents included in amounts of 5 to 25 percent weight based on the total weight of the composition. According to preferred aspects, the one or more thickening agent included in the nasal gel are selected from the group consisting of glycerin, a high molecular weight crosslinked polyacrylic acid polymer, Carboxymethylcellulose Sodium, and combinations thereof.

It will be understood by those having skill in the art that changes may be made to the details of the above-described embodiments without departing from the underlying principles presented herein. For example, the compositions disclosed herein may be administered via liquid drops from a dropper, topically (in some cases using a cotton swab or the like), orally, via a mister or atomizer, nebulization, and/or via any other suitable manner of administration. In addition, alternative compositions and treatment methods are contemplated in which the preferred nasal sprays, oral sprays or washes, and/or nasal gels may be replaced with suspensions, lozenges, tablets, capsules, topical formulations, and/or ingestible products, such as teas or other beverages, for example. In addition, any suitable combination of various embodiments, or the features thereof, is contemplated.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element.

The following aspects are disclosed in this application:

Aspect 1: A nasal or oral treatment composition comprising: at least two wetting agents, xylitol, dual salts, and an aqueous carrier, wherein application of the composition to the nasal or oral cavity for absorption by the nasal mucosa treats nasal dryness, oral dryness and allergy symptoms.

Aspect 2: The composition according to aspect 1, wherein the at least two wetting agents comprise polyethylene glycol and propylene glycol, wherein the wetting agents are provided in the composition at 10.0 wt. % to 50 wt. % based on a total wt. % of the composition.

Aspect 3: The composition according to any preceding aspect, wherein the at least two wetting agents comprise 8 wt. % to 20 wt. % polyethylene glycol and 2 wt. % to 30 wt. % propylene glycol based on a total wt. % of the composition.

Aspect 4: The composition according to any preceding aspect, wherein xylitol is provided in the composition at 0.1 wt. % to 5 wt. % based on a total wt. % of the composition.

Aspect 5: The composition according to any preceding aspect, wherein xylitol is provided in the composition at 3 wt. % to 4.5 wt. % based on a total wt. % of the composition.

Aspect 6: The composition according to any preceding aspect, further comprising a sodium salt and a potassium salt wherein the sodium salt and potassium salt comprise sodium chloride and potassium chloride each provided in the composition at 0.05 wt. % to 1.0 wt. % based on a total wt. % of the composition.

Aspect 7: The composition according to any preceding aspect, further comprising a preservative wherein the preservative comprises benzalkonium chloride or sorbic acid provided in the composition at 0.01 wt. % to 0.5 wt. % based on a total wt. % of the composition.

Aspect 8: The composition according to aspect 7, wherein the preservative comprises benzalkonium chloride provided in the composition at 0.01 wt. % to 0.3 wt. % based on a total wt. % of the composition.

Aspect 9: The composition according to any preceding aspect, wherein the aqueous carrier comprises purified water provided in the composition at 25 wt. % to 89.9 wt. % based on a total wt. % of the composition, and one or more thickening agents.

Aspect 10: The composition according to any preceding aspect, configured as a nasal or oral spray or oral rinse, wherein the one or more thickening agents comprise glycerin provided in the composition at 2 wt. % to 10 wt. % based on a total wt. % of the composition.

Aspect 11: The composition according to any one of aspects 1 to 9, configured as a nasal gel, wherein the one or more thickening agents are selected from the group consisting of glycerin, Carbopol [974P], Carboxymethylcellulose Sodium, and combinations thereof provided in the composition at 5 wt. % to 25 wt. % based on a total wt. % of composition.

Aspect 12: The composition according to any preceding aspect, further comprising at least one buffer.

Aspect 13: The composition according to aspect 11, wherein the at least one buffer is selected from the group consisting of dibasic sodium phosphate anhydrous, potassium phosphate monobasic, or a combination thereof.

Aspect 14: The composition according to any preceding aspect, having a pH of 5.5 to 7.5, such as 6.0 to 6.5, or 6.1 to 6.4.

Aspect 16: A nasal or oral treatment composition comprising: 10.0 wt. % to 50 wt. % wetting agents; 0.1 wt. % to 5 wt. % xylitol; 0.05 wt. % to 0.5 wt. % of each of a sodium salt and a potassium salt; 0.01 wt. % to 0.5 wt. % of a preservative selected from benzalkonium chloride or sorbic acid; and an aqueous carrier, wherein wt. % is based on a total wt. % of the composition, and wherein application of the composition to the nasal or oral cavity for absorption by the nasal mucosa treats nasal dryness, oral dryness and allergy symptoms.

Aspect 17: The composition according to aspect 16, wherein the wetting agents comprise 8 wt. % to 20 wt. % polyethylene glycol and 2 wt. % to 30 wt. % propylene glycol based on a total wt. % of the composition.

Aspect 18: The composition according to aspect 16 or 17, comprising 3 wt. % to 4.5 wt. % xylitol based on a total wt. % of the composition.

Aspect 19: The composition according to any one of aspects 16 to 18, configured as a nasal or oral spray or oral rinse, wherein the aqueous carrier comprises 25 wt. % to 89.9 wt. % purified water, and the composition further comprises 2 wt. % to 10 wt. % of thickening agents.

Aspect 20: The composition according to any one of aspects 16 to 18, configured as a nasal gel, wherein the aqueous carrier comprises 25 wt. % to 89.9 wt. % purified water, and the composition further comprises 5 wt. % to 25 wt. % of thickening agents, wherein the thickening agents are selected from the group consisting of glycerin, Carbopol 974P, Carboxymethylcellulose Sodium, and combinations.

Aspect 21: A method of treating nasal or oral dryness and allergy symptoms in a subject in need of such treatment, the method comprising administering to the subject the composition of any preceding aspect.

What is claimed is:

1. A nasal or oral spray composition comprising:
   3 wt. % to 15 wt. % xylitol;
   8 wt. % to 20 wt. % polyethylene glycol having a molecular weight of 3300 to 3350;
   2 wt. % to 30 wt. % propylene glycol;
   0.05 wt. % to 0.5 wt. % sodium chloride;
   0.05 wt. % to 0.5 wt. % potassium chloride;
   0.01 wt. % to 0.5 wt. % of a preservative;
   32.5 wt. % to 87 wt. % of an aqueous carrier; and
   a buffer,
   wherein the composition has a pH of 6.0 to 6.4, and wherein the wt. % is based on a total wt. % of the composition, and wherein the composition complements the sodium/potassium pump of the nose.

2. A nasal or oral gel composition comprising:
   3 wt. % to 15 wt. % xylitol;
   8 wt. % to 20 wt. % polyethylene glycol having a molecular weight of 3300 to 3350;
   2 wt. % to 30 wt. % propylene glycol;
   0.05 wt. % to 0.5 wt. % sodium chloride;
   0.05 wt. % to 0.5 wt. % potassium chloride;
   0.01 wt. % to 0.5 wt. % of a preservative;
   2 wt. % to 10 wt. % of thickening agents;
   25 wt. % to 85 wt. % of an aqueous carrier; and
   a pH adjusting agent,
   wherein the composition has a pH of 6.0 to 6.4, and wherein the wt. % is based on a total wt. % of the composition, and wherein the composition complements the sodium/potassium pump of the nose.

* * * * *